(12) United States Patent
Juillerat

(10) Patent No.: US 11,000,347 B2
(45) Date of Patent: May 11, 2021

(54) SUBASSEMBLY FOR DENTAL CARE OR SURGICAL HANDPIECE, DENTAL CARE OR SURGICAL HANDPIECE, AND ASSOCIATED ASSEMBLY METHOD

(71) Applicant: Bien-Air Holding SA, Biel (CH)

(72) Inventor: Sebastien Juillerat, Moutier (CH)

(73) Assignee: Bien-Air Holding SA, Biel (CH)

( * ) Notice: Subject to any disclaimer, the term of this patent is extended or adjusted under 35 U.S.C. 154(b) by 244 days.

(21) Appl. No.: 16/034,929

(22) Filed: Jul. 13, 2018

(65) Prior Publication Data

US 2019/0015176 A1 Jan. 17, 2019

(30) Foreign Application Priority Data

Jul. 17, 2017 (EP) ..................... 17181702

(51) Int. Cl.
*A61C 1/14* (2006.01)
*A61B 17/16* (2006.01)

(52) U.S. Cl.
CPC ............ *A61C 1/142* (2013.01); *A61B 17/162* (2013.01); *A61C 1/141* (2013.01)

(58) Field of Classification Search
CPC ........... A61C 1/142; A61C 1/14; A61C 1/141; A61C 1/144; A61C 1/145; A61C 1/08; A61C 1/12; A61C 1/00; A61B 17/162; A61B 17/00; A61B 2017/0046
See application file for complete search history.

(56) References Cited

U.S. PATENT DOCUMENTS

| | | | | |
|---|---|---|---|---|
| 5,542,846 A * | 8/1996 | Quinn | ..................... | A61C 1/141 279/106 |
| 5,836,766 A * | 11/1998 | Gugel | ..................... | A61C 1/144 433/127 |
| 8,118,594 B2 * | 2/2012 | Pernot | ..................... | A61C 1/08 433/114 |
| 9,347,319 B2 * | 5/2016 | Lai | ..................... | A61C 1/05 |
| 2009/0142730 A1 * | 6/2009 | Pernot | ..................... | A61C 1/144 433/128 |
| 2012/0189979 A1 * | 7/2012 | Tanaka | ..................... | A61C 1/141 433/127 |
| 2014/0199654 A1 * | 7/2014 | Schwarzbraun | ........ | A61C 1/12 433/127 |

FOREIGN PATENT DOCUMENTS

| | | |
|---|---|---|
| DE | 4324493 | 2/1994 |
| EP | 1378207 | 1/2004 |
| EP | 1733969 | 12/2006 |
| FR | 2873566 | 2/2006 |
| JP | 200295679 | 4/2002 |

OTHER PUBLICATIONS

European Search Report for European Patent Application No. 17181702.6, dated Feb. 1, 2018, 7 pages.

* cited by examiner

*Primary Examiner* — Jacqueline T Johanas
*Assistant Examiner* — Shannel Nicole Belk
(74) *Attorney, Agent, or Firm* — Burns & Levinson LLP; George N. Chaclas; Pegah Karimi

(57) ABSTRACT

A subassembly for a dental care or surgical handpiece comprises a push button (16) comprising a contact surface (23) adapted to receive a manual pressure able to actuate the push button (16) slidably in a sliding direction. This subassembly further comprises a piece (21) for retaining the push button (16), as well as a bayonet device (28*a*, 33, 35) able to keep assembled the push button (16) and the retaining piece (21).

16 Claims, 3 Drawing Sheets

SUBASSEMBLY FOR DENTAL CARE OR SURGICAL HANDPIECE, DENTAL CARE OR SURGICAL HANDPIECE, AND ASSOCIATED ASSEMBLY METHOD

CROSS-REFERENCE TO RELATED APPLICATION

This application claims priority to European Patent Application No. EP 17181702.6, filed Jul. 17, 2017, which is incorporated herein by reference.

TECHNICAL FIELD OF THE INVENTION

The present invention relates to the field of instruments and apparatus for practioners in the medical sector, such as dentists and surgeons. More specifically, it concerns a subassembly for a dental care or surgical handpiece, a dental care or surgical handpiece, as well as a method of assembly of the aforementioned subassembly.

STATE OF THE ART

Dentists, surgeons and other practitioners in the medical sector make use of diverse instruments and apparatus. When a tool is provided, an instrument or apparatus for a practitioner in the medical sector can be designed in such a way that this tool is removable in particular in order to be able to be replaced by another tool. When such is the case, a push button can be provided and allows a manual command to be applied for unlocking of the tool.

Proposed in each of the patent applications EP 1 378 207, DE 432 44 93 and EP 1 733 696, is a handpiece for dental or surgical use which comprises such a push button. This handpiece likewise comprises a hollow shaft associated with drive means. The tail end of a work tool, in particular a milling tool, can be mounted in this hollow shaft and be unlocked there by a device that the push button serves to actuate.

In the handpiece proposed in the patent application EP 1 378 207 among those mentioned above, the push button is retained by claws which deform elastically to allow a flange of the push button to pass during the mounting thereof. The push button of the handpiece of EP 1 378 207 cannot be removed except by damaging the claws.

In each of the handpieces proposed in the previously mentioned patent applications DE 432 44 93 and EP 1 733 696, the push button is retained by an exterior ring screwed on the body of the assembly containing the inner mechanism of the handpiece. This exterior ring can get caught and even cause injuries. Moreover, a circumferential gap coming out to the outside is present there where an edge of the exterior ring rests on the assembly body. The presence of this gap detracts from a good cleaning and an efficient disinfection of the exterior of the handpiece.

SUMMARY OF INVENTION

The subject technology has as object to allow, among other things, a push button provided on a dental care or surgical handpiece to be disassembled and there is not any gap coming out to the outside resulting from the presence of means retaining this push button.

According to the subject disclosure, this object is achieved by means of a subassembly for a dental or surgical handpiece. This subassembly comprises a push button comprising a contact surface adapted to receive a manual pressure able to actuate the push button slidably in a sliding direction. The subassembly according to the invention further comprises a piece for retaining the push button as well as a bayonet device which is able to keep assembled the push button and the retaining piece. In this bayonet device, the push button comprises a plurality of engagement portions angularly offset with respect to one another about an axis parallel to the direction of sliding and the retaining piece comprises a plurality of limit stops able to retain the engagement portions with respect to the outside, as well as a plurality of laterally open passages which pass between the limit stops, which run beyond these limit stops and the engagement portions are able to follow so as to come below the limit stops.

The subassembly defined above can incorporate one or more other advantageous features, alone or in combination, in particular from among those specified in the following.

Preferably, the push button comprises a first portion where the contact surface is located, the push button comprising a second portion which is a lateral wall closed on one side by the first portion, the first portion and the lateral wall delimiting a cavity into which penetrates at least part of the retaining piece and in which are found the limit stops and the engagement portions. When such is the case, the area of the contact surface can be maximized without changing the outer dimensions of the handpiece.

Preferably, the retaining piece is also a piece for guiding the push button in the sliding direction.

Preferably, the subassembly comprises at least one lug that a first piece between the push button and the retaining piece carries, the second piece between the push button and the retaining piece comprising at least one slide for guiding the lug in the sliding direction.

Preferably, the retaining piece comprises the slide which has an end blocked by one of the limit stops while one of the passages forms part of the retaining piece and comes out into the slide, and whereby the lug forms part of the push button, forms one of the engagement portions and is able to follow the passage coming out into the slide.

Preferably, the retaining piece comprises the slide which has an end blocked by one of the limit stops, the lug being movable in translation in the slide between a first end and an second end being located above the first end and situated at the blocked end of the slide, one of the passages forming part of the retaining piece and coming out into the slide, at a distance from the first end of the maximal course while the lug forms part of the push button, forms one of the engagement portions and is able to follow the passage coming out into the slide. When such is the case there is no risk that the push button can come apart when it is fully pushed under the action of a manual pressure. The result is increased safety, making use of the push button more reliable.

Preferably, the retaining piece comprises the slide which has an end blocked by one of the limit stops, the lug being movable in translation in the slide between a first end and an opposite second end being located above the first end and situated at the blocked end of the slide, one of the passages forming part of the retaining piece and coming out into the slide, at a distance from the first end and from the second end of the slide, while the lug forms part of the push button, forms one of the engagement portions and is able to follow the passage coming out into the slide. When such is the case, there is no risk that the push button can come apart even when it is fully pushed under the action of a manual pressure as well as when it is in its outermost position, for example under the action of a resilient element for return of this push button outwardly. The result is increased safety, making use of the push button more reliable.

Conversely, the lug can also form part of the retaining piece and form one of the limit stops, the push button comprising the slide. When such is the case, the slide advantageously has an end blocked by one of the engagement portions, a maximal course of the lug in the slide comprising a first end and a second end being located behind the first end and at the blocked end of the slide, the push button then advantageously comprising a laterally open passage that the lug is able to follow to reach the slide and which comes out into the slide, at a distance from the second end of the maximal course. When such is the case, there is no longer any risk that the push button starts to come apart when it is fully pushed under the action of a manual pressure, and the result is increased safety, making use of the push button more reliable.

Preferably, the passage coming out into the slide is formed by a first introduction part in the direction of sliding, and by a second part consisting of a lateral groove which comes out into the slide. In this way, the operation of assembly is made more intuitive and more reliable by dissociating the operation of mutual coupling from that of locking into working position by distinct manipulations, all the while in translation then in rotation in an orthogonal direction. The lateral groove constitutes moreover additional security by providing an intermediate position between a first working position where the sliding of the push button is possible and a position for disassembly of the latter.

Preferably, at least one of the passages forms part of the retaining piece and comprises an entry portion which forms a coupling slot for a tool for putting the retaining piece in place in an accommodation. In this way, this portion thus fulfils a double function, at the same time for the intrinsic bayonet device and for the mounting of this device in the handpiece.

Preferably, the retaining piece is annular and delimits axially a through opening.

Preferably, the subassembly comprises a resilient member for returning the push button outwardly.

Preferably, the retaining piece comprises a threaded portion on part of its dimension in the sliding direction.

The invention also has as object a handpiece for dental or surgical use, comprising a hole for receiving the tail end of a removable tool, as well as a device for locking this tail end of the removable tool in the hole. This handpiece comprises a subassembly as previously defined, the push button being a button for actuation of the locking device.

The handpiece for dental or surgical use defined above can incorporate one or more other advantageous features, alone or in combination, in particular from among those specified in the following.

Preferably, the handpiece comprises a rotary shaft connected to means of driving in rotation, this shaft being hollow to receive the tail end of a removable tool and being provided with a locking device which is designed to immobilize the tail end of the tool in, and with respect to, the shaft.

Preferably, the subassembly is in the prolongation of the rotary shaft, the means of driving in rotation being configured to drive the rotary shaft in a first direction of rotation, the second piece between the push button and the retaining piece comprising an entry/exit which gives access to the slide, which can be followed by the lug and which is disposed in such a way that the lug is only able to leave the slide by means of a rotation of the push button in a second direction of rotation opposite the first direction of rotation, about the axis, with respect to the retaining piece. When such is the case, the rotary shaft driven in rotation in the first direction of rotation cannot itself accidentally drive the push button in the direction of disassembly.

Preferably, the handpiece comprises an assembly body in which the retaining piece is fixed.

Preferably, the handpiece comprises an assembly body defining an elongated head which contains the shaft and at one end of which the push button is located in the prolongation of this shaft.

The invention furthermore has as object a method of assembly of a subassembly such as previously described. This method comprises steps which are:
  b) positioning the push button with respect to the retaining piece in such a way that each engagement portion is located at an entry of one of the passages (35), then
  c) by executing a manoeuvre of the push button with respect to the retaining piece in such a way that this manoeuvre includes at least a component in the direction of sliding and a component of rotation about the said axis, making the engagement portions progress in the passages until each engagement portion is brought beyond one of the limit stops.

The method of assembly described above can incorporate other advantageous features, alone or in combination, in particular from among those specified in the following.

Preferably the method of assembly comprises a step which precedes step b) and which is:
  a) screwing the retaining piece into an accommodation with the aid of a tool which is coupled to the retaining piece by engagement at least in one portion of the entry of one of the passages.

BRIEF DESCRIPTION OF DRAWINGS

Other advantages and features will follow more clearly from the description which follows of a particular embodiment of the invention, given by way of example, in a non-limiting way, and represented in the attached drawings, among which.

DESCRIPTION OF AN EMBODIMENT OF THE INVENTION

Figure 1:
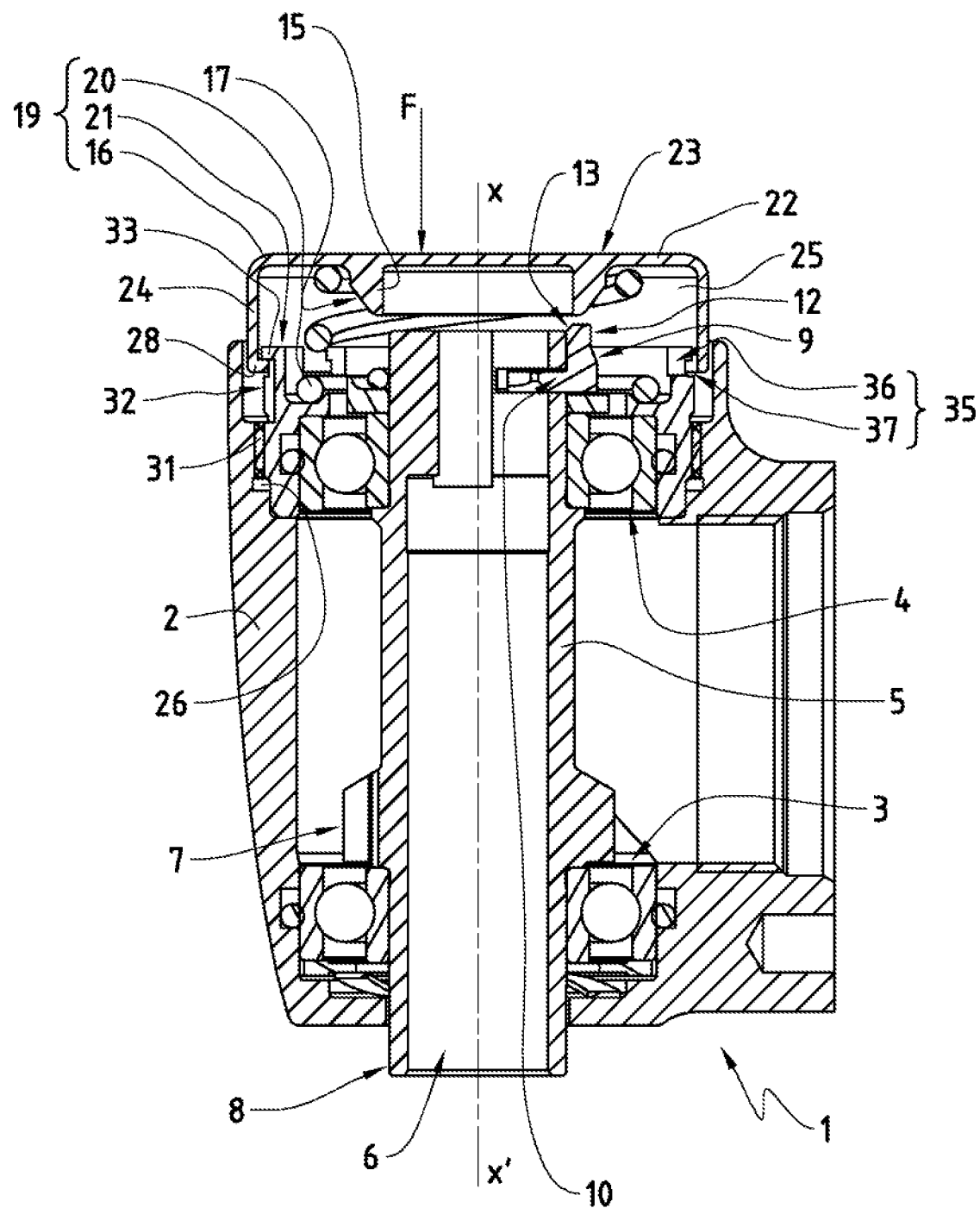
FIG. 1 is an axial sectional view of a head that a dental care or surgical handpiece comprises according to one embodiment of the subject disclosure.

FIG. 1 represents partially a dental care or surgical handpiece according to one preferred embodiment of the invention. More specifically, it represents a head 1 that this handpiece comprises and which is intended to be fixed to an end of a handle (not shown).

An assembly body 2 forms part of the outer casing of the head 1 and contains two bearings, i.e. a first bearing 3 and a second bearing 4, which together support a hollow shaft 5, rotational on an axis X-X' and delimiting a receiving hole 6 for the tail end of a removable tool (not shown). The shaft 5 comprises an annular toothing 7 intended to mesh with the toothing of a transmission element (not shown) of a drive.

Between the two opposite ends of the shaft 5, that indicated by reference numeral 8 is the open end through which a tail end of a removable tool can be introduced into the hole 6. Opposite this open end 8, the other end of the shaft 5 is provided with a device 9 for locking of the tail end of a removable tool with respect to this shaft 5. In the example represented, the locking device 9 comprises a clamping jaw 10 sliding transversely with respect to the shaft 5 and drawn back resiliently toward the axis X-X'.

The clamping jaw 10 comprises a flange 12, which has a first bevel 13 and which, thanks to the latter, can be actuated radially in the direction opposite to the axis X-X', by an inner protrusion 15 of a push button 16.

The inner protrusion 15 has the shape of an annular ridge projecting toward the bearings 3 and 4. Centered on the axis X-X', this annular ridge comprises a second bevel 17, which is intended to co-operate with the first bevel 13 when the push button 16 is actuated manually in the direction of the arrow F, parallel to the axis X-X'.

The push button 16 forms part of a subassembly 19 of the axis X-X, which also comprises a helical spring 20 and a piece 21 for retaining the push button 16 outwardly. Compressed between the retaining piece 21 and the push button 16, the helical spring 20 forms a resilient member for returning this push button 16 outwardly, in the direction contrary to that illustrated by the arrow F.

A first portion 22 of the push button 16 has the shape of a disc whose inner face bears the inner protrusion 15 and whose outer face forms a contact surface 23 adapted to receive a manual pressure in the direction of the arrow F. A second portion of the push button 16 is a tubular lateral wall 24 closed on one side by the first portion 22. The push button 16 delimits a cavity 25 into which the retaining piece 21 partially penetrates.

The retaining piece 21 is screwed into an accommodation 26 of the assembly body 2. This retaining piece 21 fulfils a plurality of functions insofar as it retains the push button 16 with respect to the outside and, moreover, insofar as it blocks the bearing 4 laterally and with respect to the outside.

Figure 2:
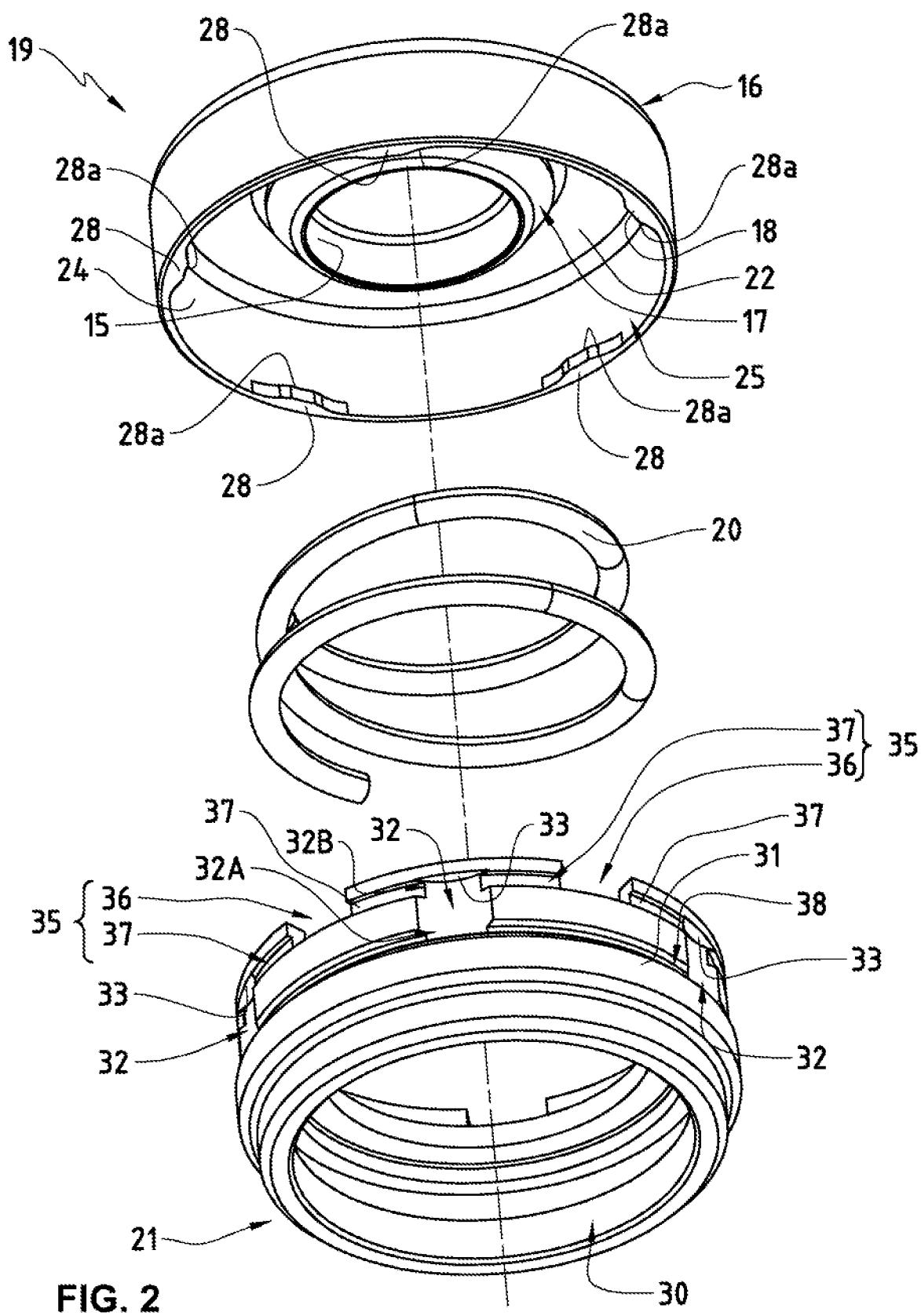
FIG. 2 is an exploded view, in perspective, of a subassembly which complies with the invention and which the dental care or surgical handpiece represented in FIG. 1 comprises.
Figure 3:
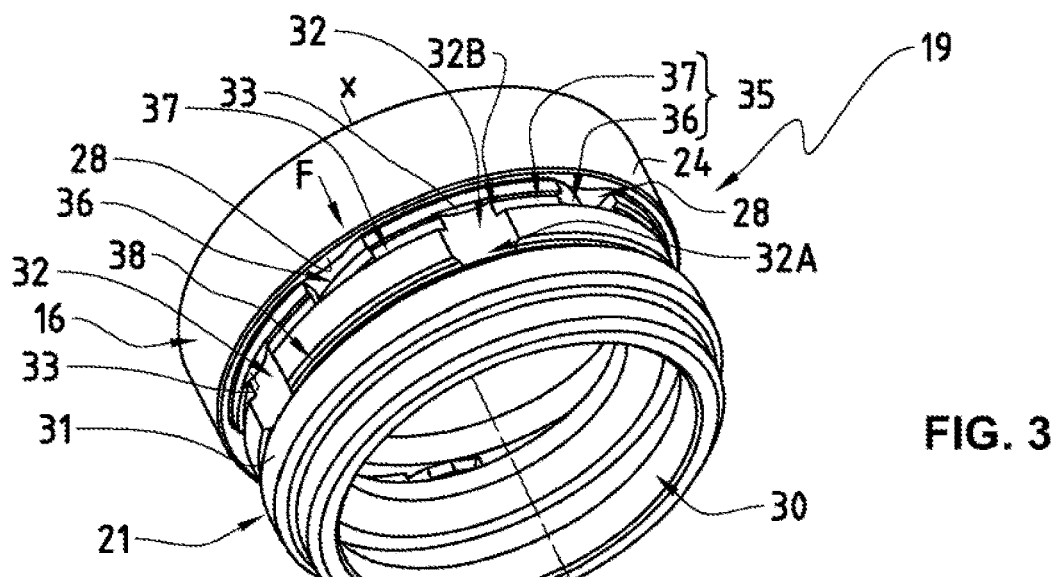
FIGS. 3 to 5 are three corresponding views in perspective and each illustrates one of the three successive steps that the assembly of the subassembly represented in FIG. 2 comprises.

The subassembly 19 is represented by itself in FIG. 2. As can be seen in this FIG. 2, the lateral wall 24 bears a plurality of inner lugs 28, which project radially inwardly and which are offset angularly with respect to one another about the axis X-X'. In the example represented, the lugs 28 each have the shape of a portion of inner flange.

The retaining piece 21 is annular and delimits a through opening 30 axially, in which an end of the shaft 5 is engaged. The retaining piece 21 comprises a threaded beading 31, thanks to which it can be mounted by screwing into the assembly body 2.

The retaining piece 21 also comprises a plurality of axial grooves, which extend parallel to the axis X-X' and which form slides 32 for guiding the lugs 28. These slides 32 are angularly offset with respect to one another about the axis X-X'. When each lug 28 is in one of the slides 32, the push button 16 is guided by the retaining piece 21 in a way so as to be able to slide in a sliding direction parallel to the axis X-X'. In other words, the retaining piece 21 of the push button 16 also constitutes a guiding piece for this push button 16. In this way, the function of guiding of the push button 16 is achieved in an autonomous way by the subassembly itself, thus advantageously dispensing with any guiding carried out by the exterior, via, for example the correspondence of form and the adjustment of the dimensions between the inner wall of the accommodation 26 and the tubular lateral wall 24. The subassembly thus formed is consequently compatible with different heads 1, the size of which and the shapes of the accommodation provided for the push button can vary slightly.

The upper end of each slide 32 is blocked in the direction of sliding in this slide 32, by a limit stop 33 constituted by a portion of outer flange of the retaining piece 21. The other end of any slide 32 is located behind the end blocked by one of the limit stops 33. It is itself blocked in the direction of sliding, by the threaded beading 31. In this way, once in the slides 32, the lugs 28 each have a maximal course limited by the threaded beading 31, constituting a first end 32A for the slide 32, and one of the limit stops 33 constituting the second end 32B for the slide 32.

Laterally open passages 35 lead to the slides 32, from the front of the retaining piece 21. Each passage 35 comprises an entry slot 36 and a lateral groove. According to the preferred embodiment illustrated in FIGS. 2 to 5, the lateral groove is a first lateral groove 37 which comes out into a slide 32, at a distance from its end blocked by the threaded beading 31. Each lateral groove 37 forms and entry/exit which gives access to a slide. Each lug 28 can follow one of the passages 35 to come beyond one of the limit stops 33. It can be noted however that a second lateral groove 38 likewise connects the lower ends of each of the slides 32, that is to say the first ends 32A of these slides.

The retaining piece 21 and the push button 16 are configured in a complementary way such that when the lugs 28 are in the passages 35, a manoeuvre of the push button in relation to the retaining piece 21 can be carried out and comprises at least one component in the direction of sliding parallel to the axis X-X' and a component of rotation about this axis X-X'. The lugs 28 and the limit stops 33 form part of a bayonet device able to keep assembled the retaining piece 21 and the push button 16. In this sense, each lug 28 forms an engagement portion 28a that a limit stop 33 is able to retain with respect to the outside, counter to the pushing exerted by the helical spring 20 in the direction contrary to the arrow F.

To mount the subassembly 19 in the assembly body 2, one starts by screwing the retaining piece 21 by itself, that is to say without the push button 16, into the assembly body 2. To do this, a tool (not shown) can be used in engagement with the edges of the slots 36, which form the slots for coupling of such a tool in addition to being entry portions of the laterally open passages 35.

Then, the push button 16 is mounted on the retaining piece 21. To do this, one begins by placing the push button 16 in front of the retaining piece 21, as it is in FIG. 3, that is to say in a way that each lug 28 is located at one of the slots 36. Then, the push button 16 is pushed in the direction of the arrow F, until each lug has reached the bottom of one of the slots 36 and is located at the same depth as the first lateral grooves 37.

Figure 4:
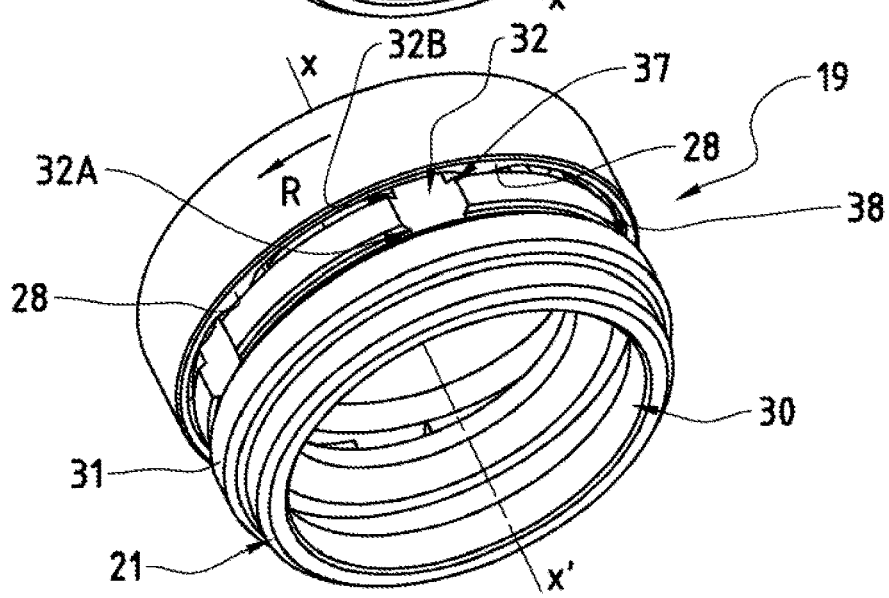
Figure 5:
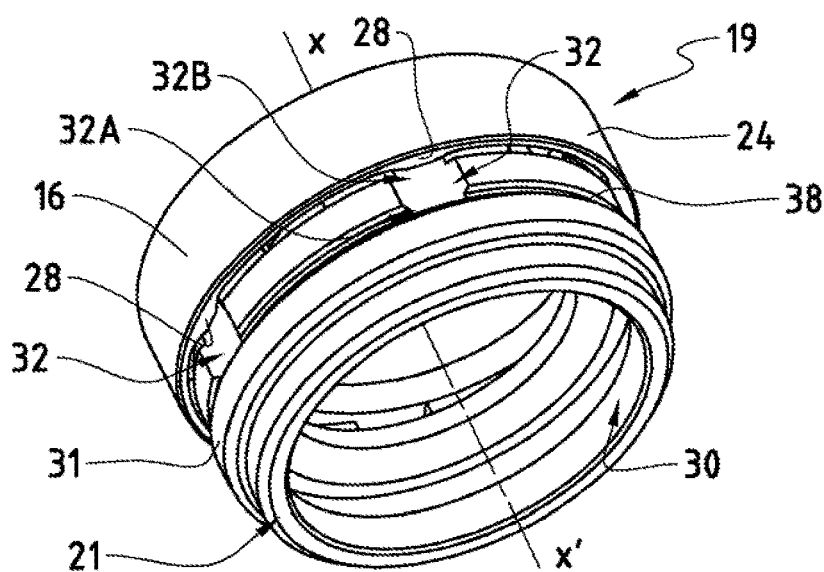

The following manoeuvre consists in making the push button 16 pivot in relation to the retaining piece 21, about the axis X-X'. It is symbolized by the arrow R in FIG. 4, illustrating a counterclockwise rotation. When each lug 28 has reached one of the slides 32 and is located behind one of the limit stops 33, the mounting of the subassembly 19 is completed.

Once in place on the retaining piece 21, the push button 16 is able to be removed. To take the push button 16 off of the retaining piece 21, the reverse procedure is used from that procedure described above used to mount the push button 16 on the retaining piece 21.

It will be understood, in view of the preceding, that the invention is not limited to the preferred embodiment described in the foregoing, which has been given only by way of example, without intending to define in an exhaustive way the scope of protection. In particular, the lugs 28 could also be borne by the retaining piece 21 and form the limit stops, while the slides 32 could be borne by the lateral wall 24 of the push button 16.

Moreover the retaining piece 21 and the assembly body 2 could also not be formed by two distinct pieces, but be combined in the form of a single monobloc piece, that is to say an integral piece.

Furthermore, the lateral wall 24 could also be less wide than the opening 30, in which case the lugs 28, the slides 32 and the limit stops 33 can be located in this opening 30.

Moreover, according to a variant, it is possible to envisage either omitting the second lateral grooves 38, or using them only instead of the first lateral grooves 37 to communicate directly with the slots 36 and to form the passages 35, thus no longer coming out into the slide 32 at its second end 32B, but at its first end 32A. However, although the operation of mounting of the push button 16 is not affected by this arrangement, an inconvenient coming apart of the latter cannot be excluded when it is actuated.

According to another variant, each passage 35 comes out into a slide 32 at a distance from the first and second ends 32A and 32B thereof, between these first and second ends 32A and 32B, that is to say not at the one nor at the other. This further reduces the risk of unfortunately coming apart of the push button 16.

According to still another variant, a single lateral groove 37 comes out into the slide 32. It then forms the sole entry/exit that the lug 28 can follow to enter this slide 32 or to exit it. When such is the case, a lug 28 can exit the slide 32 at a single entrance/exit only by means of a rotation of the push button 16 in a predefined rotational direction about the axis X-X', with respect to the retaining piece 21. This predefined direction of rotation is preferably selected in such a way as to be contrary to the direction of rotation in which the rotary shaft 5 is driven by the means of driving in rotation. In this way, the rotary shaft 5 driven in rotation cannot cause a disassembly of the push button 16.

Lastly, the locking device can have any suitable composition, which can be different from that described in the foregoing. For example, this locking device can be one of those of the handpieces described in the patent applications EP 1 378 207, DE 432 44 93 and EP 1 733 696 mentioned in the introduction.

The invention claimed is:

1. A subassembly for a dental care or surgical handpiece, comprising:
   a push button comprising a contact surface adapted to receive a manual pressure able to actuate the push button slidably in a sliding direction;
   a piece for retaining the push button; and
   a bayonet connection configured to maintain the push button and the retaining piece for retaining the push button assembled and wherein,
   the push button comprises a plurality of engagement portions angularly offset with respect to one another about an axis parallel to the sliding direction; and
   the piece for retaining the push button comprises a plurality of limit stops configured to prevent the engagement portions from move along the axis in a direction opposite the sliding direction, and a plurality of laterally open passages which positioned between the limit stops, wherein the engagement portions are positioned in a greater distance from the axis with respect to the limit stops, and the plurality of limit stops and the plurality of engagement portions form the bayonet connection.

2. The subassembly according to claim 1, wherein the push button comprises a first portion where the contact surface is located, the push button comprising a second portion which is a lateral wall closed on one side by the first portion, the first portion and the lateral wall delimiting a cavity into which penetrates at least part of the retaining piece and in which are found the limit stops and the engagement portions.

3. The subassembly according to claim 1, wherein the piece for retaining the push button is also a piece for guiding the push button in the sliding direction.

4. The subassembly according to claim 1, further comprising at least one lug that a first piece between the push button and the piece for retaining the push button carries, a second piece between the push button and the piece for retaining the push button comprising at least one slide for guiding the lug in the sliding direction.

5. The subassembly according to claim 4, wherein the piece for retaining the push button comprises the slide which has an end blocked by one of the limit stops, in that one of the passages forms part of the piece for retaining the push button and comes out into the slide, and in that the lug forms part of the push button, forms one of the engagement portions and is able to follow the passage coming out into the slide.

6. The subassembly according to claim 4, wherein the piece for retaining the push button comprises the slide which has an end blocked by one of the limit stops, the lug being movable in translation in the slide between a first end and an opposite second end being located above the first end and situated at the blocked end of the slide, one of the passages forming part of the piece for retaining the push button and coming out into the slide, at a distance from the first end of the slide, while the lug forms part of the push button, forms one of the engagement portions and is able to follow the passage coming out into the slide.

7. The subassembly according to claim 4, wherein the piece for retaining the push button comprises the slide which has an end blocked by one of the limit stops, the lug being movable in translation in the slide between a first end and an opposite second end being located above the first end and situated at the blocked end of the slide, one of the passages forming part of the piece for retaining the push button and coming out into the slide, at a distance from the first end and from the second end of the slide, while the lug forms part of the push button, forms one of the engagement portions and is able to follow the passage coming out into the slide.

8. The subassembly according to claim 5, wherein the passage coming out into the slide is formed by a first introduction part in the direction of sliding, as well as a second part consisting of a lateral groove coming out into the slide.

9. The subassembly according to claim 4, wherein the lug forms part of the piece for retaining the push button and forms one of the limit stops, the push button comprising the slide.

10. The subassembly according to claim 1, wherein at least one of the passages forms part of the piece for retaining the push button and comprises an entry portion which forms a coupling slot for a tool for putting the piece for retaining the push button in place in a housing.

11. The subassembly according to claim 1, further comprising a resilient member for returning the push button outwardly.

12. A handpiece for dental or surgical use, comprising: a hole configured to receive the tail end of a removable tool; a device configured to lock the tail end of the removable tool in the hole; and a subassembly according to claim 1, the push button being a button for actuation of the bayonet connection configured to lock.

13. The handpiece according to claim 12, further comprising a rotary shaft configured to be rotatably driven, the rotary shaft being hollow to receive the tail end of a removable tool and being provided with a locking device which is designed to immobilize the tail end of the tool in, and with respect to, the shaft.

14. The handpiece according to claim 13, further comprising at least one lug that a first piece between the push button and the piece for retaining the push button carries, a second piece between the push button and the piece for retaining the push button comprising at least one slide for guiding the lug in the sliding direction, the subassembly being in the prolongation of the rotary shaft, the rotary shaft being configured to be driven in a first direction of rotation, the second piece between the push button and the piece for retaining the push button comprising an entry/exit which gives access to the slide, which can be followed by the lug and which is disposed in such a way that the lug is only able to leave the slide by rotation of the push button in a second direction of rotation opposite the first direction of rotation, about the axis, with respect to the piece for retaining the push button.

15. The subassembly according to claim 13, wherein the device configured to lock comprises a clamping jaw sliding transversely with respect to the rotary shaft and drawn back resiliently toward the axis.

16. A method of assembly of a subassembly according to claim 1, comprising the steps which are:
   b) positioning the push button with respect to the piece for retaining the push button in such a way that each engagement portion is located at an entry of one of the passages, then;
   c) by executing a manoeuvre of the push button with respect to the piece for retaining the push button in such a way that this manoeuvre includes at least a component in the direction of sliding and a component of rotation about the said axis, making the engagement portions progress in the passages until each engagement portion is brought beyond one of the limit stops.

\* \* \* \* \*